US00PP12525P2

(12) United States Plant Patent
Bartels

(10) Patent No.: US PP12,525 P2
(45) Date of Patent: Apr. 9, 2002

(54) SOLIDAGO PLANT NAMED 'BAREIGHT'

(75) Inventor: Gosen B. H. Bartels, Aalsmeer (NL)

(73) Assignee: Bartels Breeding, B.V., Aalsmeer (NL)

( * ) Notice: Subject to any disclaimer, the term of this patent is extended or adjusted under 35 U.S.C. 154(b) by 0 days.

(21) Appl. No.: 09/655,341

(22) Filed: Sep. 5, 2000

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTITM Computer Database, 2001/02, GTI Jouve Retrieval Software, citation for 'Barieght'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Solidago plant named 'Bareight', characterized by its upright plant habit with strong stems; freely branching habit; dense and bushy growth habit; rapid growth rate; plume-like sprays of numerous dark golden yellow-colored inflorescences; excellent post-harvest longevity, typically about 14 days; and resistance to Powdery Mildew.

1 Drawing Sheet

BACKGROUND OF THE INVENTION

The present Invention relates to a new and distinct cultivar of Solidago plant, botanically known as Solidago hybrid, commercially referred to as cut Solidago, and hereinafter referred to by the cultivar name Bareight.

The new Solidago is a naturally-occurring whole plant mutation of the Solidago cultivar Kibadol, not patented. The new Solidago was discovered and selected by the Inventor in a controlled environment in Aalsmeer, The Netherlands, in 1998. The new Solidago was selected on the basis of its dark golden yellow inflorescences and excellent post-harvest longevity.

Compared to plants of the mutation parent, the cultivar Kibadol, plants of the new Solidago have darker golden yellow inflorescences and last about four days longer as cut flowers.

Asexual reproduction of the new cultivar by terminal cuttings taken at Aalsmeer, The Netherlands, has shown that the unique features of this new Solidago are stable and reproduced true to type in successive generations.

SUMMARY OF THE INVENTION

Plants of the cultivar Bareight have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Bareight'. These characteristics in combination distinguish 'Bareight' as a new and distinct cultivar:

1. Upright plant habit with strong stems.
2. Freely branching; dense and bushy growth habit.
3. Rapid growth rate.
4. Plume-like sprays of numerous dark golden-yellow-colored inflorescences.

5. Excellent post-harvest longevity, typically about 14 days.
6. Resistant to Powdery Mildew.

Plants of the new Solidago can be compared to plants of the cultivar Kibadol, not patented. In side-by-side comparisons conducted by the Inventor in Aalsmeer, The Netherlands, inflorescences of plants of the new Solidago have stronger yellow-colored ray florets and have longer post-harvest longevity than plants of the cultivar Kibadol.

Plants of the new Solidago can also be compared to plants of the cultivar Super, not patented. In side-by-side comparisons conducted by the Inventor in Aalsmeer, The Netherlands, inflorescences of plants of the new Solidago are smaller, have stronger and darker yellow-colored ray florets and have longer post-harvest longevity than plants of the cultivar Super.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Solidago. The photograph comprises a side perspective view of typical flowering stems of 'Bareight'.

DETAILED BOTANICAL DESCRIPTION

In the following description, color references are made to The Royal Horticultural Society Colour Chart except where general terms of ordinary dictionary significance are used. Plants were grown in Aalsmeer, The Netherlands, in a glass-covered greenhouse and conditions which closely approximate commercial production conditions.

Botanical classification: Solidago hybrid cultivar Bareight.
Commercial classification: Cut flower Solidago; typically used in mixed bouquets.

Parentage:

*Mutation parent.*—Solidago hybrid cultivar Kibadol, not patented.

Propagation:

*Type cutting.*—Terminal vegetative cuttings.

*Time to initiate and develop roots.*—Summer: About 7 days at 20° C. Winter: About 10 days at 18° C.

*Root description.*—Fibrous and well-branched.

Plant description:

*Crop time.*—From cuttings, about 12 weeks are required to produce a finished flowering plant.

*Form.*—Perennial herbaceous decorative cut flower plant; dense and bushy.

*Plant height, soil level to top of plant plane.*—About 1 m.

*Plant diameter or spread.*—About 37.5 cm.

*Growth rate.*—Rapid growth rate.

*Branching habit.*—Freely branching with about four lateral branches per plant; removal of terminal apices (pinching) enhances branching.

*Lateral branches.*—Length: About 1 m. Diameter: About 1 cm. Internode length: About 2 cm. Strength: Very strong, flexible. Texture: Smooth; slightly pubescent.

*Foliage description.*—Leaves simple, alternate, generally symmetrical and long persisting. Tolerant to stresses. Quantity per lateral branch: Typically about 40. Length: About 12 cm. Width: About 2 cm. Shape: Narrowly oblong. Apex: Sharply acute. Base: Attenuate. Margin: Dentate. Venation pattern: Pinnate. Texture: Leathery; smooth. Color: Young foliage, upper surface: 139A. Young foliage, lower surface: 137A. Mature foliage, upper surface: 139A; venation, 139A. Mature foliage, lower surface: 137A; venation, 137A. Petiole: Length: About 1 cm. Diameter: About 2 mm. Color: 139A.

Inflorescence description:

*Inflorescence type and habit.*—Numerous spike-like panicles, plume-like; panicles pyramidal in shape. Ray and disc florets arranged acropetally on a capitulum. Freely flowering, about 500 inflorescences per plant. Inflorescences persistent. Not fragrant.

*Flowering response.*—Under natural conditions, plants flower in the late summer/early autumn. At other times of the year, inflorescence initiation and development can be induced under short day/long night conditions. Response time is about 5 to 6 weeks.

*Post-production longevity.*—Excellent, cut flowers maintain good post-harvest longevity for typically about 14 days. On the plant, inflorescences maintain good substance for about 3 weeks.

*Panicle length.*—About 15 cm.

*Panicle diameter.*—About 15 cm.

*Inflorescence diameter.*—About 5 mm.

*Inflorescence depth (height).*—About 2 mm.

*Disc diameter.*—About 2 mm.

*Inflorescence buds (just showing color).*—Length: About 2 mm. Diameter: About 1 mm. Shape: Cylindrical. Rate of opening: Rapid. Color: 4A.

*Ray florets.*—Number per inflorescence: About 10 or 12 in one row. Length: About 2 mm. Width: About 1 mm. Shape: Oblong. Apex: Typically acute. Base: Attenuate. Margin: Entire. Texture: Smooth, glabrous. Aspect: About 45 to 90° from vertical. Color: Upper surface, when opening and fully opened: 4A. Lower surface, when opening and fully opened: 4A.

*Disc florets.*—Number per inflorescence: About 10. Length: About 2 mm. Diameter: Less than 1 mm. Shape: Tubular. Color: Immature: 6A. Mature: 6A.

*Involucral bracts.*—Number per inflorescence: About 8 to 10. Shape: Deltoid. Apex: Sharply acute. Texture: Smooth. Color, upper and lower surfaces: 137B.

*Peduncles.*—Strength: Strong. Angle: About 40° to the stem. Length: First (terminal) peduncle: About 3 mm. Fourth peduncle: About 5 mm. Seventh peduncle: About 7 mm. Texture: Smooth. Color: 137B.

*Reproductive organs.*—Androecium: Present on disc florets only. Anther size: Less than 0.5 mm. Pollen amount: Abundant. Pollen color: 9B. Gynoecium: Present on both ray and disc florets. Pistil length: About 0.5 mm.

*Seed.*—Seed production has not been observed.

Disease resistance: Plants of the new Solidago have been noted to be resistant to Powdery Mildew under commercial production conditions.

It is claimed:

1. A new and distinct cultivar of Solidago plant named 'Bareight', as illustrated and described.

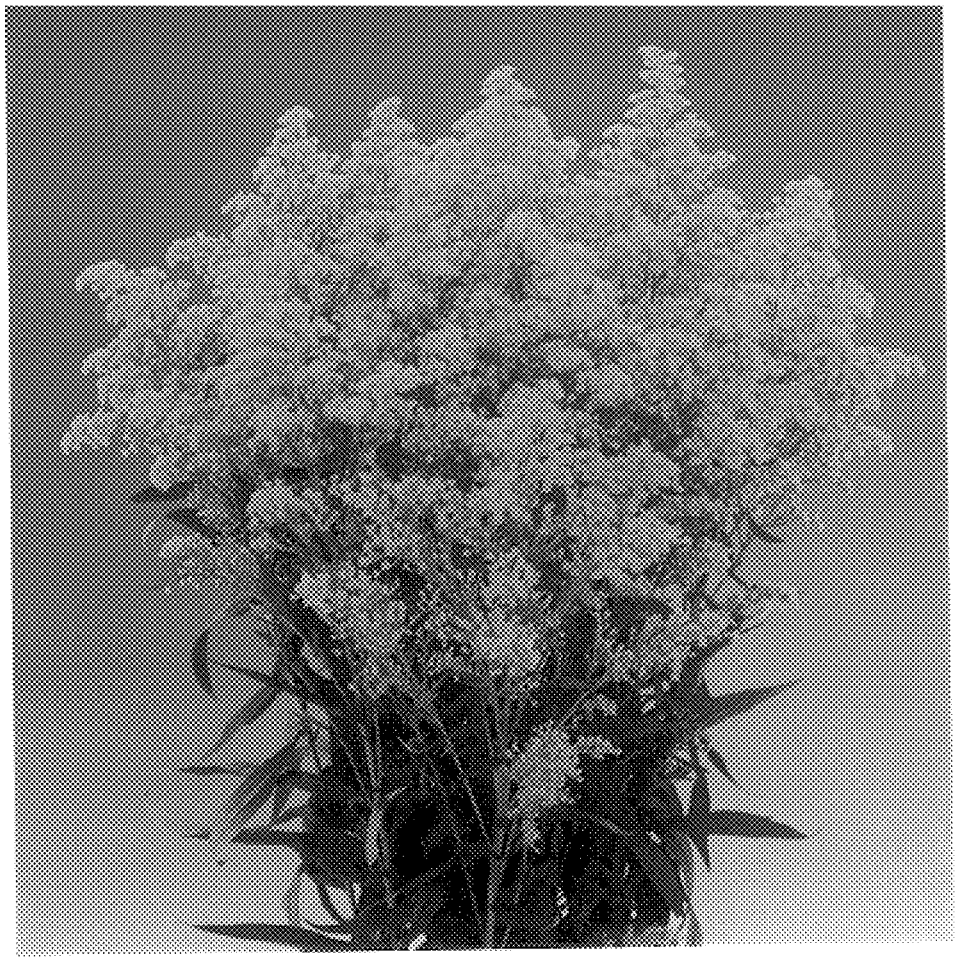

* * * * *